(12) United States Patent
Runchevski et al.

(10) Patent No.: US 12,208,076 B2
(45) Date of Patent: Jan. 28, 2025

(54) MECHANOSYNTHESIS OF A CO-AMORPHOUS FORMULATION OF CREATINE WITH CITRIC ACID AND HUMIDITY-MEDIATED TRANSFORMATION INTO A CO-CRYSTAL

(71) Applicant: Southern Methodist University, Dallas, TX (US)

(72) Inventors: Tomche Runchevski, Dallas, TX (US); Kyle B. Pekar, Corpus Christi, TX (US); Jonathan B. Lefton, Fort Worth, TX (US)

(73) Assignee: Southern Methodist University, Dallas, TX (US)

( * ) Notice: Subject to any disclaimer, the term of this patent is extended or adjusted under 35 U.S.C. 154(b) by 740 days.

(21) Appl. No.: 17/484,420

(22) Filed: Sep. 24, 2021

(65) Prior Publication Data
US 2022/0087966 A1  Mar. 24, 2022

Related U.S. Application Data

(60) Provisional application No. 63/082,651, filed on Sep. 24, 2020.

(51) Int. Cl.
| | | |
|---|---|---|
| *A61K 31/205* | (2006.01) | |
| *A23L 2/52* | (2006.01) | |
| *A61K 47/54* | (2017.01) | |
| *C07C 59/265* | (2006.01) | |
| *C07C 279/14* | (2006.01) | |

(52) U.S. Cl.
CPC .......... *A61K 31/205* (2013.01); *A61K 47/542* (2017.08)

(58) Field of Classification Search
CPC .. A61K 31/205; A61K 47/542; C07C 279/14; C07C 59/265; C07B 2200/13; A23L 2/52
See application file for complete search history.

(56) References Cited

U.S. PATENT DOCUMENTS

| | | | |
|---|---|---|---|
| 6,211,407 B1 | 4/2001 | Thomson | |
| 7,109,373 B2 | 9/2006 | Boldt | |
| 7,150,880 B2 | 12/2006 | Howard et al. | |
| 7,608,641 B2 | 10/2009 | Miller et al. | |
| 9,486,424 B2 | 11/2016 | Miller et al. | |
| 10,376,521 B2 * | 8/2019 | Zaworotko | C07D 401/14 |
| 10,435,356 B1 | 10/2019 | Kramer et al. | |
| 10,485,777 B1 | 11/2019 | Kramer et al. | |
| 10,555,921 B1 | 2/2020 | Kramer et al. | |
| 2002/0131987 A1 | 9/2002 | Carnazzo | |
| 2004/0077719 A1 | 4/2004 | Jager et al. | |
| 2004/0133040 A1 | 7/2004 | Boldt | |
| 2005/0037069 A1 | 2/2005 | Purpura et al. | |

FOREIGN PATENT DOCUMENTS

WO    WO-02052957 A1  *  7/2002  .......... A23L 33/175

OTHER PUBLICATIONS

Korde, S., S. Pagire, H. Pan, C. Seaton, A. Kelly, Y. Chen, Q. Wang, P. Coates, and A. Paradkar, "Continuous Manufacturing of Cocrystals Using Solid State Shear Milling Technology", Cryst. Growth Des. (2018), 18: pp. 2297-2304 (Year: 2018).*
English translation of WO 02/052,957 A1, https://patents.google.com/patent/WO2002052957A1/en?oq=WO02052957, Assessed on Jul. 23, 2024. (Year: 2024).*
Aakeröy, C. B.; Fasulo, M. E.; Desper, J. Cocrystal or Salt: Does It Really Matter? Mol. Pharmaceutics 2007, 4, 317-322.
Alonzo, D. E.; Zhang, G. G. Z.; Zhou, D.; Gao, Y.; Taylor, L. S. Understanding the behavior of amorphous pharmaceutical systems during dissolution. Mol. Pharmaceutics 2010, 27, 608-618.
Andreev, Y. G.; MacGlashan, G. S.; Bruce, P. G. Ab initio solution of a complex crystal structure from powder-diffraction data using simulated-annealing method and a high degree of molecular flexibility. Phys. Rev. B: Condens. Matter Mater. Phys. 1997, 55, 12011-12017.
Andronis, V.; Yoshioka, M.; Zografi, G. Effects of Sorbed Water on the Crystallization of Indomethacinfrom the Amorphous State. J. Pharm. Sci. 1997, 86, 346-351.
Arlin, J.-B.; Bhardwaj, R. M.; Johnston, A.; Miller, G. J.; Bardin, J.; MacDougall, F.; Fernandes, P.; Shankland, K.; David, W. I. F.; Florence, A. J. Structure and stability of two polymorphs of creatine and its monohydrate. Cryst. Eng. Comm. 2014, 16, 8197-8204.
Babu, N. J.; Nangia, A. Solubility Advantage of Amorphous Drugs and Pharmaceutical Cocrystals. Cryst. Growth Des. 2011, 11, 2662-2679.
Becke, A. D. Density-Functional Exchange-Energy Approximation with Correct Asymptotic Behavior. Phys. Rev. A 1988, 38, 3098-3100.
Bethune, S. J.; Huang, N.; Jayasankar, A.; Rodriguez-Hornedo, N. Understanding and Predicting the Effect of Cocrystal Components and pH on Cocrystal Solubility. Cryst. Growth Des. 2009, 9, 3976-3988.
Bolla, G.; Nangia, A. Pharmaceutical cocrystals: walking the talk. Chem. Commun. 2016, 52, 8342-8360.
Braga, D.; Mainia, L.; Grepioni, F. Mechanochemical preparation of co-crystals. Chem. Soc. Rev. 2013, 42, 7638-7648.
Braun, D. E.; Orlova, M.; Griesser, U. J. Creatine: Polymorphs Predicted and Found. Cryst. Growth Des. 2014, 14, 895-4900.
Cheary, R. W.; Coelho, A. A.; Cline, J. P. Fundamental parameters line profile fitting in laboratory diffractometers. J. Res. Natl. Inst. Stand. Technol. 2004, 109, 1-25.

(Continued)

*Primary Examiner* — Samantha L Shterengarts
*Assistant Examiner* — Sagar Patel
(74) *Attorney, Agent, or Firm* — Edwin S. Flores; Daniel J. Chalker; Chalker Flores, LLP

(57) ABSTRACT

The present invention includes a co-crystal of creatine and citric acid obtained by milling, methods of making the same that include a process for the preparation of co-amorphous formulation of creatine and citric acid, the process comprising: mixing creatine and citric acid; milling the creatine and citric acid for a time sufficient to form a co-amorphous solid, which co-amorphous solid can be converted into a co-crystal, and nutritional supplements that include the same.

5 Claims, 4 Drawing Sheets

(56) References Cited

OTHER PUBLICATIONS

Civalleri, B.; Zicovich-Wilson, C. M.; Valenzano, L.; Ugliengo, P. B3LYP Augmented with an Empirical Dispersion Term (B3LYP-D*) as Applied to Molecular Crystals. Cryst. Eng. Commun. 2008, 10, 405-410.

Coelho, A. A. Indexing of powder diffraction patterns by iterative use of singular value decomposition. J. Appl. Crystallogr. 2003, 36, 86-95.

Cruz-Cabeza, A. J. Acid-base crystalline complexes and the pKa rule. Cryst. Eng. Commun. 2012, 14, 6362-6365.

Dengale, S. J.; Grohganz, H.; Rades. T.; Löbmann, K. Recent advances in co-amorphous drug formulations. Ad. Drug Delivery Rev. 2016, 100, 116-125.

Dinnebier, R. E. Rigid bodies in powder diffraction. A practical guide. Powder Diffr. 1999, 14, 84-92.

Dovesi, R.; Erba, A.; Orlando, R.; Zicovich-Wilson, C. M.; Civalleri, B.; Maschio, L.; Rerat, M.; Casassa, S.; Baima, J.; Salustro, S.; Kirtman, B. Quantum-Mechanical Condensed Matter Simulations with CRYSTAL. WIREs Comput. Mol. Sci. 2018, 8, e1360.

Duggirala, N. K.; Perry, M. L.; Zaworotko, M. J. Pharmaceutical cocrystals: along the path to improved medicines. Chem. Commun. 2016, 52, 640-655.

Erba, A.; Maul, J.; Civalleri, B. Thermal Properties of Molecular Crystals Through Dispersion-Corrected Quasi-Harmonic Ab Initio Calculations: The Case of Urea. Chem. Commun. 2016, 52, 1820-1823.

Etter, M. C. Encoding and decoding hydrogen-bond patterns of organic compounds. Acc. Chem. Res. 1990, 23, 120-126.

Friščić, T. Supramolecular concepts and new techniques in mechanochemistry: cocrystals, cages, rotaxanes, open metal-organic frameworks. Chem. Soc. Rev. 2012, 41, 3493-3510.

Friščić, T.; Mottillo, C.; Titi, H. M. Mechanochemistry for Synthesis. Angew. Chem. Int. Ed. 2020, 59, 1018-1029.

Good, D. J.; Rodriguez-Hornedo. N. Solubility Advantage of Pharmaceutical Cocrystals. Cryst. Growth Des. 2009, 9, 2252-2264.

Halasz, I.; Puškarić, A.; Kimber, S. A. J.; Beldon, P. J.; Belenguer, A. M.; Adams, F.; Honkimäki, V.; Dinnebier, R. E.; Patel, B.; Jones, W.; Štrukil, V.; Friščić, T. Real-Time In Situ Powder Xray Diffraction Monitoring of Mechanochemical Synthesis of Pharmaceutical Cocrystals. Angew. Chem. Int. Ed. 2013, 125, 11752-11755.

Hancock, B. C.; Zografi, G. The Relationship between the Glass-Transition Temperature and the Water-Content of Amorphous Pharmaceutical Solids. Pharm. Res. 1994, 11, 471-477.

Hasa, D.; Rauber, G. S.; Voinovich, D.; Jones, W. Cocrystal Formation through Mechanochemistry: from Neat and Liquid-Assisted Grinding to Polymer-Assisted Grinding. Angew. Chem. Int. Ed. 2015, 127, 7479-4783.

Jaeger, R.; Purpura, M.; Shao, A.; Inoue, T.; Kreider, R. B. Analysis of the efficacy, safety, and regulatory status of novel forms of creatine. Amino Acids 2011, 40, 1369-1383.

Jayasankar, A.; Good, D. J.; Rodríguez-Hornedo, N. Mechanisms by Which Moisture Generates Cocrystals. 2007, 4, 360-372.

Karki, S.; Friščić, T.; Jones, W.; Motherwell, W. D. S. Screening for Pharmaceutical Cocrystal Hydrates via Neat and Liquid-Assisted Grinding. Mol. Pharmaceutics 2007, 4, 347-354.

Kohn, W.; Sham, L. J. Self-Consistent Equations Including Exchange and Correlation Effects. Phys. Rev. 1965, 140, A1133-A1138.

Kreider, R. B. Effects of creatine supplementation on performance and training adaptations. Mol. Cell. Biochem. 2003, 244, 89-94.

Lee, C.; Yang, W.; Parr, R. G. Development of the Colle-Salvetti Correlation-Energy Formula into a Functional of the Electron Density. Phys. Rev. B 1988, 37, 785-789.

Lu, Q.; Zografi, G. Properties of Citric Acid at the Glass Transition. J. Pharm. Sci. 1997, 86, 1374-1378.

Mendel, H; Hodgkin D. C. The crystal structure of creatine monohydrate. Acta Crystallogr. 1954, 7, 443-446.

Monkhorst, H. J.; Pack, J. D. Special Points for Brillouin-zone Integrations. Phys. Rev. B 1976, 13, 5188-5192.

Pawley, G. S. Unit-cell refinement from powder diffraction scans. J. Appl. Crystallogr. 1981, 14, 357-361.

Peintinger, M. F.; Oliveira, D. V.; Bredow, T. Consistent Gaussian Basis Sets of Triple-Zeta Valence with Polarization Quality for Solid-State Calculations. J. Comput. Chem. 2012, 34, 451-459.

Pirttimaki, J.; Laine, E. The Transformation of Anhydrate and Hydrate Forms of Caffeine at 100-Percent RH and 0-Percent RH. Eur. J. Pharm. Sci. 1994, 1, 203-208.

Rietveld, H. M. A profile refinement method for nuclear and magnetic structures. J. Appl. Crystallogr. 1969, 2, 65-71.

Runčevski, T.; Petruševski, G.; Makreski, P.; Ugarkovic, S.; Dinnebier, R. E. On the hydrates of codeine phosphate: the remarkable influence of hydrogen bonding on the crystal size. Chem. Commun. 2014, 50, 6970-6972.

Sander, J. R. G.; Buar, D.-G.; Henry, R. F.; Zhang, G. G. Z.; MacGillivray, L. R. Pharmaceutical nano cocrystals: sonochemical synthesis by solvent selection and use of a surfactant. Angew. Chem. Int. Ed. 2010, 49, 7284-7288.

Schultheiss, N.; Newman, A. Pharmaceutical Cocrystals and Their Physicochemical Properties. Cryst. Growth Des. 2009, 9, 2950-2967.

Seefeldt, K.; Miller, J.; Alvarez-Núñez, F.; Rodriguez-Hornedo, N. Crystallization Pathways and Kinetics of Carbamazepine-Nicotinamide Cocrystals from the Amorphous State by in-Situ Thermomicroscopy, Spectroscopy and Calorimetry Studies. J. Pharm. Sci. 2007, 96, 1147-1158.

Surov, A. O.; Voronin, A. P.; Vener, M. V.; Churakov, A. V.; Perlovich, G. L. Specific Features of Supramolecular Organisation and Hydrogen Bonding in Proline Cocrystals: A Case Study of Fenamates and Diclofenac. Cryst. Eng. Commun. 2018, 20, 6970-6981.

Merck Index Online. 2020. [online] Available at: <https://www.rsc.org/merck-index> (Accessed Sep. 16, 2020).

Trask, A. V. An Overview of Pharmaceutical Cocrystals as Intellectual Property. Mol. Pharmaceutics 2007, 4, 301-309.

Weyna, D. R.; Shattock, T.; Vishweshwar, P.; Zaworotko, M. J. Synthesis and Structural Characterization of Cocrystals and Pharmaceutical Cocrystals: Mechanochemistry vs Slow Evaporation from Solution. Cryst. Growth Des. 2009, 9, 1106-1123.

Wyss, M; Kaddurah-Daouk R. Creatine and Creatinine Metabolism. Physiological Rev. 2000, 80, 1107-1213.

Yoshinari, Y.; Forbes, R. T.; York, P.; Kawashima, Y. Moisture Induced Polymorphic Transition of Mannitol and Its Morphological Transformation. Int. J. Pharm. 2002, 247, 69-77.

Jayasankar, A.; Somwangthanaroj, A.; Shao, Z. J.; Rodríguez-Hornedo, N. Cocrystal Formation During Cogrinding and Storage is Mediated by Amorphous Phase. Pharm. Res. 2006, 23, 2381-2392.

International Search Report and Written Opinion for PCT/US2021/051963 by the USPTO dated Feb. 8, 2022, 11 pp.

Pekar, et al., "Mechanosynthesis of a Coamorphous Formulation of Creatine with Citric Acid and Humidity-Mediated Transformation into a Cocrystal," Crystal Growth & Design, 2021, 21, pp. 1297-1306.

* cited by examiner

MECHANOSYNTHESIS OF A CO-AMORPHOUS FORMULATION OF CREATINE WITH CITRIC ACID AND HUMIDITY-MEDIATED TRANSFORMATION INTO A CO-CRYSTAL

CROSS-REFERENCE TO RELATED APPLICATIONS

This application claims priority to U.S. Provisional Application Ser. No. 63/082,651, filed Sep. 24, 2020, the entire contents of which are incorporated herein by reference.

TECHNICAL FIELD OF THE INVENTION

The present invention relates in general to the field of nutritional supplements, and more particularly, to the mechanosynthesis of a co-amorphous formulation of creatine with citric acid and humidity-mediated transformation into a co-crystal.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with nutritional supplementation.

Creatine, N-(aminoiminomethyl)-N-methyl glycine, is a naturally produced compound that functions as an intermediary for the phosphagen energy system in humans and other vertebrates.[1] Numerous studies have shown that supplemented creatine is an excellent ergogenic aid reported to significantly enhance both anaerobic exercise capacity and maximal power/strength performance during sets of maximal-effort muscle contractions and single-effort sprints.[2] Expectedly, its popularity as a fitness supplement soared among athletes and fostered a market currently valued at $350-550 million in the US alone. The most frequently marketed form, creatine monohydrate, was introduced in the early 1990s as an oral supplement consumed via dissolution in beverages. In this regard, creatine monohydrate, even with its overwhelming market share, still has a significant drawback due to its rather modest aqueous solubility (13.3 g/L).[3] Creatine hydrochloride was recently introduced as an alternative supplement formulation with drastically increased aqueous solubility (≥150 g/L).[4] Characterized by a strong acidic aftertaste, the high degree of acidity associated with hydrochloride salts can adversely impact dental health. This surge in popularity, in conjunction with explosive growth of the sports supplement industry, motivated the development and eventual presentation of novel formulations of creatine. Several of these alleged forms have been reported without proper characterization and remain questionable in their collective legal/regulatory status.[5]

Thus, a need remains for nutritional supplementation with creatine that is soluble and does not have such high acidity that is adversely impacts dental health.

SUMMARY OF THE INVENTION

In one embodiment, the present invention includes a co-crystal of creatine and citric acid obtained by milling. In one aspect, the co-crystal has a powder X-ray diffraction (PXRD) diffractogram which peaks at ±3 in °2θ are of a structure with a unit cell parameters a=23.79 Å, b=5.23 Å, c=11.87 Å, $\alpha$=90°, $\beta$=78.5°, $\gamma$=90° and space group $P2_1/c$, with selected peaks at °2θ of 1.72, 3.47, 6.85, 6.97, 8.55, 8.71, collected using X-ray radiation with 0.7 Å wavelength. In another aspect, the co-crystal has a PXRD diffractogram substantially similar to the PXRD diffractogram is depicted in FIG. 1 collected using an X-ray radiation with 0.7 Å wavelength. In another aspect, the co-crystal has a DSC thermogram comprising an endothermic peak with a peak onset of approximately 115° C. and a peak maximum of about 126° C., similar to the DSC thermogram is depicted in FIG. 6. In another aspect, the co-crystal has an IR spectrum is depicted in FIG. 2C. In another aspect, the creatine is creatine base, creatine anhydrate, creatine in zwitterionic form or creatine hydrate with molar amount of water from 0 to 5. In another aspect, the citric acid is citric acid anhydrate, or citric acid hydrate with molar amount of water from 0 to 5. In another aspect, a molar ratio of creatine and citric acid is approximately 0.9:1.1, 1:1, or 1.1:0.9. In another aspect, the co-crystal comprises sufficient water to produce, stabilize, or both, the co-crystal.

A process for the preparation of co-amorphous formulation of creatine and citric acid, the process comprising: mixing creatine and citric acid; milling the creatine and citric acid for a time sufficient to form a co-amorphous solid. In one aspect, the co-crystal has an IR spectrum is depicted at FIG. 2C. In another aspect, the co-crystal has a powder X-ray diffraction (PXRD) diffractogram shows amorphous material, and is depicted in FIG. 2A. In another aspect, the co-crystal has a DSC thermogram comprising an exothermic peak with a peak onset of approximately 90° C. and a peak minimum of about 102° C., followed by an endothermic peak with a peak onset of approximately 120° C. and a peak minimum of about 135° C. is depicted in FIG. 6. In another aspect, water is added during the milling process to allow for direct synthesis of a co-crystal. In another aspect, a liquid assisted milling is achieved with a solvent other than water. In another aspect, the co-crystal has a powder X-ray diffraction (PXRD) diffractogram which peaks at ±3 in °2θ are of a structure with a unit cell parameters a=23.79 Å, b=5.23 Å, c=11.87 Å, $\alpha$=90°, $\beta$=78.5°, $\gamma$=90° and space group $P2_1/c$, with selected peaks expressed in °2θ, at 1.72, 3.47, 6.85, 6.97, 8.55, 8.71, collected using X-ray radiation with 0.7 Å wavelength. In another aspect, the co-crystal has a PXRD diffractogram substantially similar to the PXRD diffractogram is depicted in FIG. 1 collected using X-ray radiation with 0.7 Å wavelength. In another aspect, the co-crystal has a DSC thermogram comprising an endothermic peak with a peak onset of approximately 115° C. and a peak maximum of about 126° C., depicted in FIG. 6. In another aspect, the co-crystal has an IR spectrum is depicted in FIG. 2C. In another aspect, the creatine is creatine base, creatine anhydrate, creatine in zwitterionic form or creatine hydrate with molar amount of water from 0 to 5. In another aspect, the citric acid is citric acid anhydrate, or citric acid hydrate with molar amount of water from 0 to 5. In another aspect, the creatine and citric acid comprises an amount of citric acid with respect to creatine at a molar ratio of 0.9:1.1, 1:1, or 1.1:0.9. In another aspect, the milling is a stirred media mill, an attrition mill, a planetary ball mill, or a ball mill. In another aspect, a milling media is steel, chrome steel, stainless steel, ceramic, or rubber. In another aspect, the milling is between 1 and 60 minutes, is between 1 and 60 Hz, or both. In another aspect, the process further comprising exposing the amorphous solid to humidity to transform into a co-crystal. In another aspect, a molar ratio of creatine and citric acid is approximately 0.9:1.1, 1:1, or 1.1:0.9. In another aspect, the milling is at a temperature of between about 0° C. and about 120° C.

A process for the preparation of a co-crystal of creatine and citric acid, the process comprising: mixing a creatine in the form of a creatine base, a creatine anhydrate, a creatine in zwitterionic form or a creatine hydrate with molar amount of water from 0 to 5 with citric acid; and milling the creatine and citric acid for a time sufficient to form the co-crystal. In one aspect, the citric acid anhydrate with molar amount of water from 0 to 5. In another aspect, both creatine and citric acid are hydrates with molar amount of water from 0 to 5. In another aspect, the creatine and citric acid comprises an amount of citric acid with respect to creatine at a molar ratio of 0.9:1.1, 1:1, or 1.1:0.9. In another aspect, the milling is a stirred media mill, an attrition mill, a planetary ball mill, or a ball mill. In another aspect, a milling media is steel, chrome steel, stainless steel, ceramic, or rubber. In another aspect, the milling is between 10 and 60 minutes, is between 10 and 60 Hz, or both. In another aspect, the co-crystal has a powder X-ray diffraction (PXRD) diffractogram which peaks at ±3 in °2θ are of a structure with a unit cell parameters a=23.79 Å, b=5.23 Å, c=11.87 Å, α=90°, β=78.5°, γ=90° and space group P2$_1$/c, with selected peaks expressed in °2θ, at 1.72, 3.47, 6.85, 6.97, 8.55, 8.71, collected using X-ray radiation with 0.7 Å wavelength. In another aspect, the co-crystal has a PXRD diffractogram substantially similar to the PXRD diffractogram depicted in FIG. 1 collected using X-ray radiation with 0.7 Å wavelength. In another aspect, the co-crystal has a DSC thermogram is depicted in FIG. 6. In another aspect, the co-crystal has an IR spectra is depicted in FIG. 2C. In another aspect, the citric acid is citric acid anhydrate, or citric acid hydrate with molar amount of water from 0 to 5. In another aspect, a molar ratio of creatine and citric acid is approximately 0.9:1.1, 1:1, or 1.1:0.9. In another aspect, the milling is at a temperature of between about 0° C. and about 120° C.

A nutritional supplement comprising co-crystal, co-amorphous, or both, of creatine and citric acid with molar ratio of water from 0 to 5. In another aspect, the co-crystal has a powder X-ray diffraction (PXRD) diffractogram which peaks (±3 in °2θ) are of a structure with a unit cell parameters a=23.79 Å, b=5.23 Å, c=11.87 Å, α=90°, β=78.5°, γ=90° and space group P2$_1$/c, with selected peaks expressed in °2θ, at 1.72, 3.47, 6.85, 6.97, 8.55, 8.71, collected using X-ray radiation with 0.7 Å wavelength. In another aspect, the co-crystal has a PXRD diffractogram substantially similar to the PXRD diffractogram depicted in FIG. 1 collected using X-ray radiation with 0.7 Å wavelength. In another aspect, the co-crystal has a DSC thermogram comprising an endothermic peak with a peak onset of approximately 115° C. and a peak maximum of about 126° C., similar to the DSC thermogram is depicted in FIG. 6. In another aspect, the co-crystal has an IR spectrum comprising of peaks at 2 C. In another aspect, the creatine is creatine base, creatine anhydrate, creatine in zwitterionic form or creatine hydrate with molar amount of water from 0 to 5. In another aspect, the citric acid is citric acid anhydrate, or citric acid hydrate with molar amount of water from 0 to 5. In another aspect, the molar ratio of creatine and citric acid is approximately 1:1. In another aspect, an unreacted reactant is water at a molar ratio of 0 to 5. In another aspect, the nutritional supplement further comprises one or more: proteins, amino acids, vitamins, minerals, carbohydrates, or lipids. In another aspect, the nutritional supplement further comprises one or more additives selected from colorant, stabilizer, thickener, flavoring, sweetener, anti-foaming agents, binding agents, bulking agents, glidants, lubricants, flavoring agents, release modifying agents, and preservatives.

BRIEF DESCRIPTION OF THE DRAWINGS

For a more complete understanding of the features and advantages of the present invention, reference is now made to the detailed description of the invention along with the accompanying figures and in which:

(FIG. 2A) PXRD patterns and (FIG. 2B) IR spectra of the co-amorphous solid, a-CCA (blue lines) and the co-crystal, c-CCA (green lines). The PXRD patterns and IR spectra of milled samples of phase-pure creatine anhydrate, CA, and phase-pure citric acid anhydrate, CAA, are shown for reference (black lines), and (FIG. 2C) IR are spectra of the co-amorphous (blue lines) and the co-crystal (green lines).

(FIG. 3A) TGA curves of c-CAA measured directly after milling (black line) and after drying of the sample for 24 h at room temperature (green line). (FIG. 3B) TGA curves of a-CAA (blue line) and c-CAA (green line). The TGA curves of phase-pure creatine anhydrate and phase-pure citric acid anhydrate are shown for reference (black dotted lines).

DETAILED DESCRIPTION OF THE INVENTION

Figure 1:
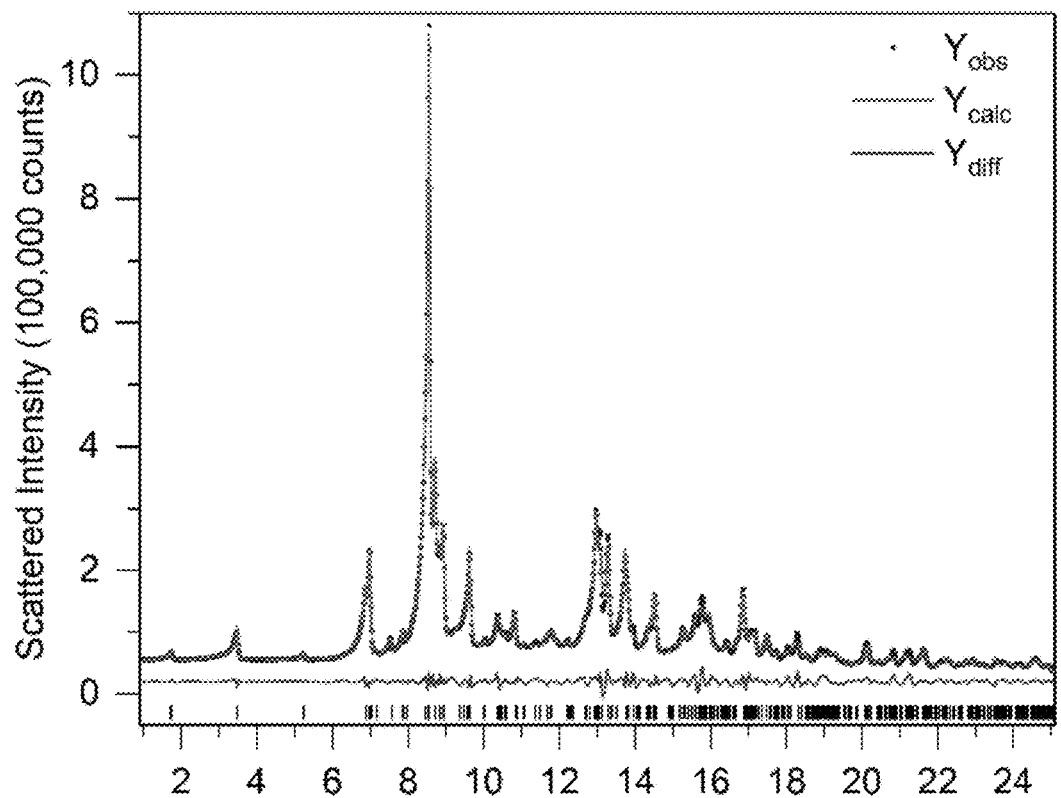
FIG. 1 shows a powder diffraction pattern and Rietveld refinement plot for the co-crystal. Measured scattered X-ray intensity is presented as blue dots, the simulated pattern is presented as a red line, and the difference curve between the measured and simulated patterns is presented as a green, Bragg reflections are given as blue bars (X-ray λ=0.7093 Å).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention relates in general to the field of nutritional supplements, and more specifically, to the mechanosynthesis of a co-amorphous formulation of creatine with citric acid and humidity-mediated transformation into a co-crystal.

As used herein, the term "nutritional supplement(s)" refers to substances or formulations that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional supplement(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

Non-limiting examples of vitamins, minerals and/or other compounds for use with the present invention can be selected from the group consisting of vitamin A, fat soluble vitamins, B vitamins, B-complex vitamins and analogs thereof, vitamin C, vitamin D, vitamin E, folic acid, calcium, iron, magnesium, phosphorus, potassium, zinc, manganese, sodium, copper, iodine, molybdenum, selenium, chlorides, phosphate salts and chromium, choline, inositol, vitamin K, vitamin C, thiamin, riboflavin, niacin, vitamin B6, folate, vitamin B12, biotin, pantothenic acid, potassium, calcium, magnesium, iron, zinc, copper, manganese, selenium, chromium, molybdenum, iodine, sodium, sulfur, phosphorus, docosahexaenoic acid, eicosapentaenoic acid, arachidonic acid, and lutein, and salts, chelates, and esters thereof.

Non-limiting examples of amino acids are selected from the group consisting of essential amino acids, non-essential amino acids, creatine monohydrate, HMB, AKIC, OKG, pyroglutamic acid, 4-hydroxyisoleucine, and DMAE.

Non-limiting examples of carbohydrates selected from the group consisting of ribose, dextrose, dietary fiber, maltodextrin, fructose, pyruvates, and glucosamine.

Non-limiting examples of bulking agents can include, e.g., lactose, sucrose, dextrose, sorbitol, fructose, and cellulose powder.

Non-limiting examples of disintegrating agents can include, e.g., microcrystalline cellulose, starches, crospovidone, sodium starch glycolate, and crosscarmellose sodium.

Non-limiting examples of a glidant or lubricant agents can include, e.g., talc, corn starch, silicon dioxide, sodium lauryl sulfate, magnesium stearate, calcium stearate, sodium stearate, stearic acid, sodium stearyl fumarate, hydrogenated cotton seed oil, talc, waxes, cetyl alcohol, glyceryl stearate, glyceryl palmitate, glyceryl behenate, hydrogenated vegetable oils, and stearyl alcohol.

Non-limiting examples of taste-masking agents can include, e.g., cellulose hydroxypropyl ethers (HPC); low-substituted hydroxypropyl ethers (L-HPC); cellulose hydroxypropyl methyl ethers (HPMC); methylcellulose polymers; Ethylcelluloses (EC) and mixtures thereof; Polyvinyl alcohol (PVA); hydroxyethylcelluloses; carboxymethylcelluloses and salts of carboxymethylcelluloses (CMC); polyvinyl alcohol and polyethylene glycol co-polymers; monoglycerides, triglycerides, polyethylene glycols, modified food starch, acrylic polymers and mixtures of acrylic polymers with cellulose ethers; cellulose acetate phthalate; sepifilms such as mixtures of HPMC and stearic acid, cyclodextrins, and mixtures thereof.

Non-limiting examples of flavoring agents can include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, or a combination thereof.

Non-limiting examples of release modifying agents can include, e.g., ethylcellulose, glyceryl dibehenate, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, stearyl alcohol, acrylic acid copolymers, sodium alginate, carrageenan, alginic acid, pectin, sodium carboxymethyl cellulose, a starch derivative, or a combination thereof.

Non-limiting examples of binding agents can include, e.g., polyvinyl pyrrollidone, starch, methylcellulose, hydroxypropyl methylcellulose, carboxymethyl cellulose, sucrose solution, dextrose solution, guar gum, xanthan gum, acacia, tragacanth, locust bean gum and sodium alginate, or an alginic acid salt.

Non-limiting examples of preservatives can include, e.g., potassium sorbate, sodium sorbate, potassium benzoate, sodium benzoate, calcium disodium EDTA, and mixtures thereof.

Scheme 1. Structural formulas of creatine and citric acid.

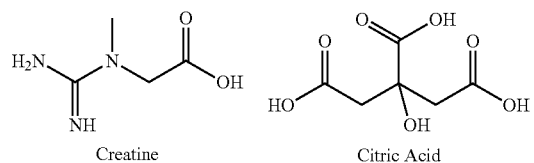

Creatine          Citric Acid

The present inventor designed a new creatine formulation with increased solubility. The formation of co-crystals with biocompatible, highly soluble counterparts can be implemented to enhance the aqueous solubility of creatine, improving consumer appeal and efficacy as a drug. Similarly, the preparation of co-amorphous solids has shown to be a new and potent crystal-engineering strategy for increasing the solubility and stability of pharmaceuticals. In this regard, mechanochemistry has emerged as a valuable tool for the preparation of new solid-state formulations.[19-25] Creatine features carboxylic and guanidino functional groups (Scheme 1), both of which are available for acid-base chemistry and co-crystal formation. The propensity of this small molecule to engage in co-crystal formation was tested with various co-crystal counterparts. The screening experiments indicate that creatine does not readily form co-crystals. The inventors attribute this to the possibility of proton transfer between the carboxylic and guanidino functional groups and the formation of strong intermolecular interactions between creatine zwitterions, as observed in creatine polymorphs and hydrates.[7-9] While traditional solvothermal methods resulted in precipitation of physical mixtures containing creatine and counterpart, the inventors found that mechanochemical synthesis of creatine with citric acid (Scheme 1) allowed for the unique synthesis of a 1:1 formulation. Citric acid is known to undergo glass transition upon cooling from a melt.[26] The inventors hypothesize that, given its propensity to form a disordered solid, citric acid may be a good candidate for a co-amorphous/glassy formulation with creatine, which can be later transformed into a co-crystal. It was found that milling of both compounds in dry conditions gave a co-amorphous solid (a-CCA), whereas milling in the presence of small amounts of water (via creatine hydrate, citric acid hydrate, or catalytic drop) yielded a co-crystal (c-CAA). Furthermore, a-CCA is stable under dry conditions, but readily converts to c-CCA upon contact with ambient humidity. Herein, the inventors show these intriguing processes and their associated solid-state structures and physicochemical properties, determined by using a combination of complementary methods: high-resolution powder X-ray diffraction (PXRD), infrared (IR) spectroscopy, thermogravimetric analysis (TGA), differential scanning calorimetry (DSC), nuclear magnetic resonance (NMR) spectroscopy, and density functional theory (DFT) methods.

Materials. Creatine monohydrate (GNC), citric acid anhydrate (Fisher), and citric acid monohydrate (Fisher) were purchased and used as received without further purification. Their purity was checked by NMR prior to usage. Creatine anhydrate was prepared by dehydration of creatine monohydrate at 373 K for 3 h and confirmed with TGA. The anhydrous forms were stored in a desiccator.

Mechanosynthesis of a-CCA. Creatine anhydrate (131 mg, 1.00 mmol) and citric acid anhydrate (192 mg, 1.00 mmol) were transferred to a stainless-steel milling canister along with one stainless-steel ball bearing (4.0 g). The sample was milled for 30 min at 30 Hz, resulting in a fine, chalky powder, which was transferred to a drybox under a nitrogen atmosphere.

Mechanosynthesis of c-CCA. Creatine monohydrate (149 mg, 1.00 mmol) and citric acid anhydrate (192 mg, 1.00 mmol) were transferred to a stainless-steel milling canister along with one stainless-steel ball bearing (4.0 g). The mixture was milled for 30 min at 30 Hz, yielding a wet solid which was removed to dry on the benchtop for 24 h, resulting in a dry solid. Similar procedures were repeated using creatine anhydrate milled with citric acid monohydrate and creatine monohydrate milled with citric acid monohydrate, resulting in the same crystalline product as confirmed by PXRD.

PXRD. The PXRD patterns were collected on a high-resolution laboratory Stoe Stadi-P powder diffractometer, operating in Debye-Scherrer (transmission) geometry. The diffractometer was equipped with a molybdenum X-ray source. Monochromatic Mo-K$\alpha_1$ radiation was obtained by a primary Ge(111) monochromator (centered at 0.7093 Å). Scattered X-ray intensity was simultaneously collected by two highly sensitive, linearly positioned silicon-strip (Mythen Dectris 1K) detectors. Sample preparation involved very gentle grinding of the materials in a pestle and packing in borosilicate capillaries with 0.5 mm diameter. During measurements, the capillary was rotated for improved particle statistics. Diffraction data was collected at room temperature. Typically, diffraction patterns were collected in the 0-25°2θ range for 2 h. The diffraction pattern used for structure solution and refinement was collected for 24 h.

Crystal Structure Solution and Refinement. The powder diffraction pattern of c-CAA (FIG. 1) was analyzed with the TOPAS-Academic V6 (Coelho Software, 2018) software. The indexing of the pattern was performed by the singular value decomposition function.[27] The indexing indicated a monoclinic unit cell, with a probable P2$_1$/c space group symmetry (later confirmed by a Rietveld[28] refinement). Precise unit cell parameters were obtained by structureless Pawley fitting,[29] using the fundamental parameter approach.[30] During the Pawley fitting iterations, unit cell parameters, background coefficients (described as a Chebyshev polynomial of 10$^{th}$ order), and parameters describing both the peak profile and instrumental contribution (using the simple axial model) were simultaneously varied. Once the fitting converged, the crystal structure solution process was initiated using precise unit cell parameters and a P2$_1$/c symmetry and completed by the real-space global optimization approach of simulated annealing using the Metropolis algorithm.[31] To decrease the degrees of freedom, rigid bodies described in a Z-matrix notation were utilized.[32] Based on the asymmetric unit volume, one creatine molecule and one citric acid molecule were used in the structure solution process. Considering the possibilities of proton transfer, as well as the conformational flexibility of the carboxylate group, hydrogen atoms were not included in the initial model (except for the hydrogens bound to aliphatic carbon atoms). To account for the small excess of electron density from the hydrogen atoms, the occupancy factors of the terminal oxygen atoms were set flexible within the 1-1.1 range. During the simulated annealing runs, bond distances and angles associated with the rigid bodies were kept fixed, whereas all possible dihedral angles were set flexible. The rigid bodies were freely translated and rotated in the asymmetric unit. Once the optimization converged to a global minimum, the model was subjected to whole-pattern Rietveld refinement.[2] Hydrogen atoms were added based on geometric considerations. During the refinement, all of the aforementioned parameters were refined, in addition to unit cell parameters, peak shape and profile parameters, background coefficients (described as a Chebyshev polynomial), bond lengths and angles within the rigid bodies (applying soft constraints), and thermal displacement parameters (defined as a single variable for each atomic type, except for hydrogen atoms, which were calculated as the thermal displacement parameter of the bonded atom multiplied by a factor of 1.5). The refinement converged quickly with satisfactory figures of merit and a sufficient difference curve.

The Rietveld plot is given in FIG. 1, and selected parameters and figures of merit are presented in Table 1.

TABLE 1

Selected Structural, Crystallographic and X-ray Powder Diffraction Data for c-CAA.

| | c-CAA |
|---|---|
| λ (Å) | 0.7093 |
| T (K) | 293 |
| °2θ range | 1-25 |
| Time (h) | 24 |
| molecular formula | $C_4H_9N_3O_2{:}C_6H_8O_7$ |
| crystal system | Monoclinic |
| space group | $P2_1/c$ |
| a (Å) | 23.836 (4) |
| b (Å) | 5.229 (1) |
| c (Å) | 11.835 (2) |
| α (°) | 90 |
| β (°) | 78.25 (1) |
| γ (°) | 90 |
| V (Å) | 1444.3 (5) |
| Z | 1 |
| $R_{exp}$ (%)[a] | 0.02 |
| $R_p$ (%)[a] | 3.25 |
| $R_{wp}$ (%)[a] | 4.33 |
| $R_{Bragg}$ (%)[a] | 1.03 |
| No. of variables | 104 |

[a]The figures of merit are as defined in TOPAS-Academic V6.

Theoretical Calculations. Geometry optimizations and vibrational frequency calculations for creatine, citric acid, and their co-crystal were carried out utilizing density functional theory (DFT) with periodic boundary conditions,[33] based on the B3LYP functional[34,35] augmented with a modified empirical dispersion term (B3LYP-D*).[36] The B3LYP-D* functional was chosen for its strength in adequately accounting for electron correlation in crystalline systems and describing noncovalent interactions including hydrogen bonding.[37,38] The pob-TZVP Gaussian-type basis set of triple-ζ quality was employed for describing C, H, O, and N.[39] All DFT calculations were performed with the Crystal17 program package.[40] Geometry optimizations including a full relaxation of both atomic positions and lattice parameters were carried out using the Monkhorst-Pack[41] grid of 10×10×8 in combination with the convergence criteria of $10^{-7}$ for the Coulomb and exchange integrals. Harmonic vibrational frequencies and corresponding normal modes were calculated at the center of the Brillouin zone (Γ point)[41] to ensure that the relaxed structures correspond to local energy minima.

IR Spectroscopy. Infrared (IR) spectra were collected with a Fourier transform infrared (FTIR) Thermo Fisher Nicolet iS50 spectrometer. The samples were prepared by grinding 1 mg of sample with 100 mg of KBr and then pressing into a pellet.

TGA. The thermogravimetric analysis (TGA) of creatine anhydrate (CA), citric acid anhydrate (CAA), a-CCA, and c-CCA was performed with a Netzsch TG 209 F3 Tarsus instrument. Each sample was placed in an alumina crucible and heated from 25 to 1000° C. at a heating rate of 10° C./min under a constant flow of nitrogen.

DSC measurements for a-CCA and c-CCA were performed on a Netzsch DSC 214 Polyma instrument in hermetically sealed aluminum pans, heated from 30 to 140° C. at a rate of 10° C./min under a constant flow of nitrogen.

NMR Spectroscopy. All $^1$H-NMR spectra were collected on a Jeol 500 MHz spectrometer with a variable temperature probe. Experiments were setup with a 45° pulse and 10 s relaxation delay, with 16 scans per measurement.

Solubility Measurements. The aqueous solubility of creatine monohydrate and c-CCA was determined via NMR spectroscopy. The samples were weighed such that the maximum achievable concentration was 0.50 M. NMR tubes were prepared by first adding the creatine monohydrate (45 mg) or c-CCA (58 mg), followed by 600 μL of the internal standard solution. The NMR tube was vigorously shaken with a Vortex 2 Genie to form a suspension, which was then settled with the aid of centrifugation. NMR experiments were then measured with a relaxation delay of 10 s, allowing for 15-min dissolution periods after raising the temperature. The dissolved content was measured at 25, 35, 45, and 55° C.

Figure 2A:
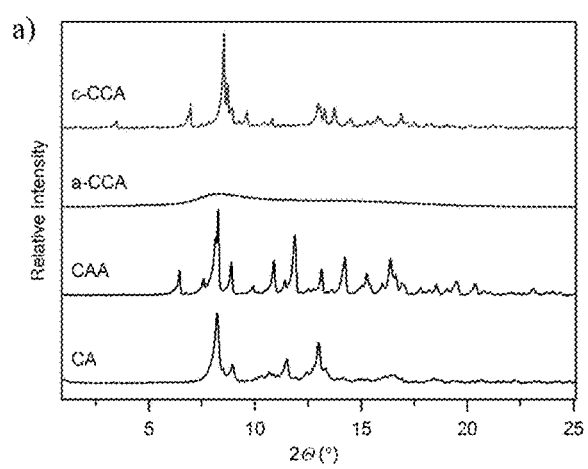
FIGS. 2A to 2C show.

Mechanosynthesis and characterization of a-CCA. The present inventors attempted to co-crystalize creatine with various coformers by solvatothermal methods, but were unsuccessful. Numerous crystallizations at various conditions resulted in polycrystalline mixtures. In fact, creatine is poorly soluble in various solvents, limiting the design of a broad screening procedure. Therefore, the inventors turned to mechanochemistry as an alternative strategy for co-crystal screening. A primary target was co-crystallization of creatine with citric acid—a food-grade and inexpensive chemical that can be used to alter various physicochemical properties of solid-state formulations, such as solubility and taste. Ball milling of equimolar amounts of creatine anhydrate with citric acid anhydrate led to a supramolecular reaction and formation of a co-amorphous formulation, a-CAA. The powder diffraction pattern of a-CAA, shown in FIG. 2A, features a complete disappearance of Bragg peaks and presence of a broad halo from 4 to 20 °2θ with X-ray scattering maximum at 8 °2θ. As a control experiment, the inventors performed ball milling of phase-pure creatine anhydrate and phase-pure citric acid anhydrate. As shown in FIG. 2A, neither of these experiments resulted in a polymorphic phase transition or amorphization.

Figure 2B:
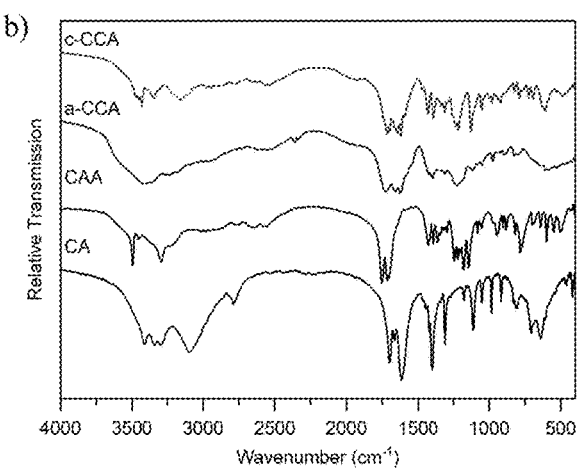
Figure 2C:
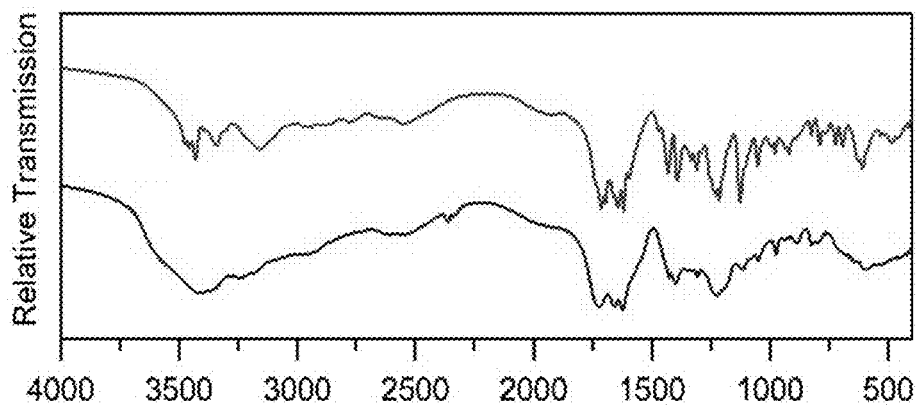

To gain further insight into the local structure product obtained by milling, the sample was studied using IR spectroscopy. FIG. 2B presents the IR spectrum of the amorphous sample, together with the IR spectra of samples of phase-pure creatine anhydrate and citric acid anhydrate, prepared under identical conditions. The spectrum of the milled sample has markedly different spectral features compared to the spectra of the pure compounds. Expectedly, the spectrum of the co-amorphous formulation features a significant peak broadening and loss of fine structure, both of which are concomitants of the loss of long-order periodicity of the crystal structure. In a-CCA, each creatine and citric acid building block has a slightly different local structure that leads to a different local environment around the vibrating atoms, hence giving rise to red/blue shifts and broadening of the corresponding IR peaks. FIG. 2C shows an IR arc spectra of the co-amorphous (blue lines) and the co-crystal (green lines).

Figure 3A:
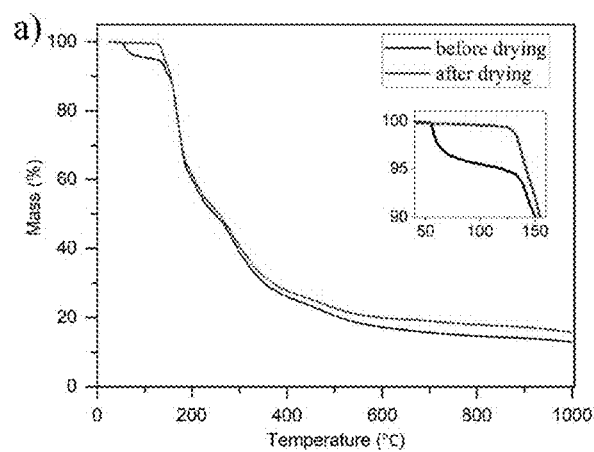
FIGS. 3A and 3B show.

The thermal analysis of a-CAA indicated that the co-amorphous material is stable up to a temperature of 129° C., as shown in FIG. 3A. The decomposition temperature of a-CAA is significantly lower than the decomposition temperatures of phase-pure creatine anhydrate (220° C.) and citric acid anhydrate (164° C.). The decomposition profile features two consecutive steps, which can be assigned to the decomposition of one equivalent of citric acid, followed by the decomposition of one equivalent of creatine, confirming the expected 1:1 stoichiometry. The different thermal decomposition pattern of a-CAA further supports the hypothesis that the milling product is a co-amorphous formulation and not a physical mixture of amorphous starting materials.

Mechanosynthesis and characterization of c-CCA. Small, catalytic amounts of liquids can dramatically change the course of a mechanochemical reaction and lead to the formation of different products.[21-26] The inventors were particularly interested in studying the effect of water on the milling reaction, as water molecules can be incorporated into solid formulations to form the corresponding hydrates.[25, 42] Additionally, water can serve as an agent for liquid assisted grinding (LAG).[23] The inventors tested different strategies for introducing water molecules into the milling reaction. First, creatine anhydrate and citric acid anhydrate were milled together with 0.056 µL of water per mg of sample (typical LAG). Second, water was introduced in a crystalline form, as compositional part of either creatine monohydrate, citric acid monohydrate or both. Regardless of the origin of the water molecules, the mechanochemical reactions consistently resulted in a highly crystalline product. The powder diffraction patterns of this product, c-CAA, are presented in FIG. 1. and FIG. 2A. Close inspection of the pattern revealed that the material exists as a single phase, without detectable amounts of crystalline phases of creatine and/or citric acid.

Figure 3B:
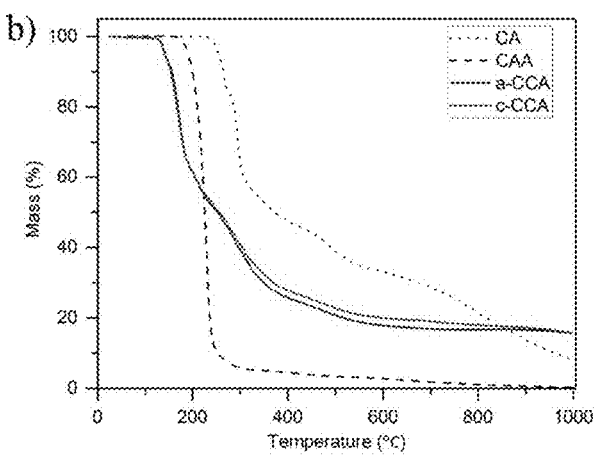

Thorough spectroscopic and thermal analyses indicated that the crystalline product is an anhydrous co-crystal of creatine and citric acid, c-CAA, with 1:1 stoichiometry. The IR spectrum of c-CAA is remarkably similar to the IR spectrum of a-CAA, shown in FIG. 2B and FIG. 2C. The similarity between the IR spectra of both formulations points to similarities in their local structures and is indicative of a 1:1 stoichiometry. This stoichiometry was confirmed by thermal analyses. The TGA profile of c-CAA features a small mass loss (~4.8%) at low temperature (57° C.), which is characteristic for a loss of physisorbed water molecules. This water content can be rapidly removed by drying the material on the benchtop for over 24 h, as shown in FIG. 3A. The similar TGA profiles of dried c-CAA and a-CAA, shown in FIGS. 3A and 3B, further confirm that the co-amorphous and the co-crystalline formulation have the same stoichiometry and similar local structures.

Figure 4:
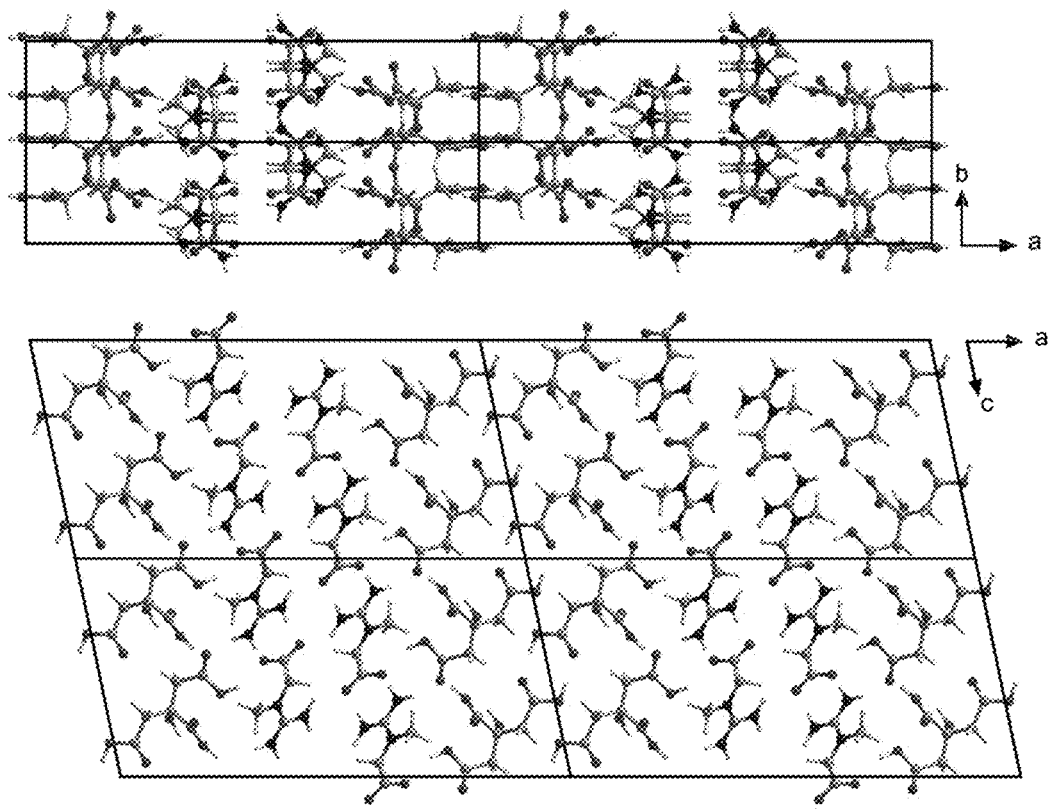
FIG. 4 shows a crystal-packing diagram of c-CCA presented along the c-crystallographic axis (upper panel) and the b-crystallographic axis (upper panel). The packing is presented with four unit cells. Hydrogen, carbon, oxygen and nitrogen atoms are represented with white, gray, red and blue, respectively.

Crystal Structure Description of c-CAA. The structure and stoichiometry of c-CAA were proven by detailed structural analyses. The high crystallinity and phase purity of the material allowed for ab initio crystal structure solution and Rietveld refinement from the PXRD data. The Rietveld refinement revealed that the c-CCA co-crystal adopts an ordered structure that can be described in the monoclinic $P2_1/c$ space group. The asymmetric unit consists of one creatine and one citric acid counterpart. The crystal packing, shown in FIG. 4, features creatine and citric acid double layers, repeating in the direction of the a-crystallographic axis. In the creatine double layer, each creatine interacts with three symmetrically equivalent creatine molecules, with hydrogen bonding with the carboxylic and guanidino functional groups, establishing two $R_2^2(8)$ and one $R_2^2(14)$ supramolecular graph sets,[43] in addition to various intermolecular chains, $C_2^2$, and rings $R_6^6$ (not shown). The close intermolecular oxygen . . . nitrogen contacts (2.73(5) Å, 2.72(8) Å and 2.90(5) Å, FIG. 4) indicate strong hydrogen bonds between symmetrically equivalent molecules. Similarly, in the citric acid double layer, each citric acid molecule interacts with five symmetrically equivalent molecules, with the carboxylic functional groups forming one typical $R_2^2(8)$ synthon (with a close oxygen . . . oxygen contact of 2.66(8) Å) and several intermolecular chains ($C_1^1$, $C_2^2$ and $C_4^4$ graph set notation) as well as $R_6^6$ intermolecular rings (not shown). The creatine and citric acid double layers are connected by two hydrogen bonds, one between the carboxylic groups of creatine and citric acid (oxygen . . . oxygen, 2.9(2) Å) and another, weaker one between the guanidino group and the carboxylic group (nitrogen . . . oxygen, 3.1(7) Å). The hydrogen bonding scheme of creatine and citric acid is dominated by discrete, finite hydrogen-bonding patterns, forming various $D_1^1$, $D_2^3$, $D_3^2$, $D_3^3$ graph sets, in addition to a $C_2^2$ intermolecular chain (not shown).

In order to inspect the stability of the experimental crystal structure, the inventors performed detailed DFT energy calculations, using the B3LYP-D* functional. As a control study, the inventors performed identical geometry optimizations on the reported crystal structures of creatine monohydrate and citric acid. The geometry optimizations of each structure confirmed that the experimental models are energetically stable. Small deviations are observed in regard to the unit cell parameters; these can be assigned to the presence of strain and stress in the crystal structures, which are not accounted for by the theoretical calculations. Importantly, the overall crystal packing, and particularly the hydrogen-bonding network, are found to be in excellent agreement between experiment and theory.

Figure 5:
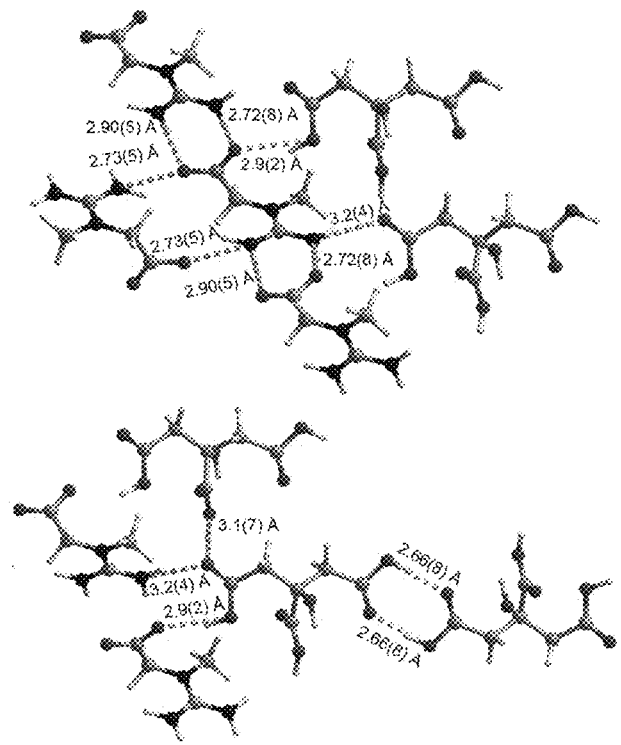
FIG. 5 shows selected hydrogen-bonding pattern around the a) creatine and b) citric acid in the structure of c-CCA. Hydrogen bonds are presented with dotted yellow bonds. Hydrogen, carbon, oxygen and nitrogen atoms are shown in white, gray, red and blue, respectively.

Accurate classification of a solid-state formulation as a salt or as a co-crystal can impact the interpretation of the physicochemical properties[44] and inform future application of crystal engineering strategies as well as patenting procedures.[45] Creatine and citric acid can form both a co-crystal and a salt. Due to intrinsic limitations of the method, laboratory PXRD cannot be used to detail the position of the hydrogen atoms in the structure; however, salt/co-crystal characterization can be successfully performed by considering the supramolecular synthons and the $pK_a$ rule.[46] Citric acid has $pK_{a1}$=3.13, $pK_{a2}$=4.76 and $pK_{a3}$=6.39, whereas creatine has $pK_{a1}$=3.5 and $pK_{a2}$=12.46. An interaction between the guanidino group of creatine and a carboxylic group of citric acid ($\Delta pK_a$=9.33) would result in formation of salt, whereas interaction between the carboxylic groups would result in a co-crystal. Inspection of the hydrogen-bonding pattern in the structure of c-CAA clearly outlines a $R_2^2(8)$ synthon between symmetrically equivalent creatine molecules, with $\Delta pK_a$=8.96 and relatively close oxygen . . . nitrogen distances of 2.72(8) Å and 2.90(5) Å (FIG. 5). It is safe to assume that the carboxylic groups of creatine can protonate neighboring guanidino groups and form creatine zwitterions. At the same time, the interaction between the guanidino group of creatine and the carboxylic group of citric acid is comparatively weaker, as evidenced by a significantly longer nitrogen . . . oxygen distance of 3.1(7) Å. Furthermore, the presence of a $R_2^2(8)$ synthon between two creatine molecules excludes the possibility of a simultaneous presence of a protonated carboxylic and protonated guanidino groups proving that the formulation is a co-crystal and not a salt.

Co-amorphous-to-Co-crystal Transformations. An intrinsic characteristic of amorphous solids is their lower stability compared to their thermodynamically most stable crystalline counterparts. Therefore, the inventors investigated the stability of the a-CAA as a function of temperature and humidity.

Figure 6:
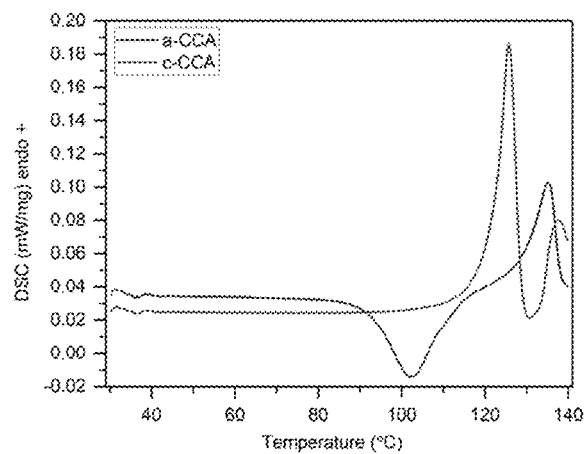
FIG. 6 shows the DSC thermograms of the co-amorphous (blue lines, a-CCA) and the co-crystal (green lines, c-CCA), showing melting at 126° C., crystallization at 102° C., and melting at 135° C.

FIG. 6 presents the DSC curves of a-CAA and c-CAA collected from 30 to 140° C. c-CAA is characterized by a melting endothermic peak centered at 126° C. and a thermal decomposition peak centered at 138° C., complementary to the TGA results. Heating of a-CAA leads to two distinct thermal events. First, an exothermic event is observed at 102° C. associated with crystallization of the co-amorphous phase. Second, the crystalline phase undergoes melting at 135° C., followed by thermal decomposition. Considering the similar thermal decomposition profiles of a-CAA and c-CAA (FIG. 3A), the inventors hypothesized that heating of a-CAA leads to crystallization into a co-crystal with a crystal structure closely related to c-CAA. Variable-temperature PXRD experiments, as well as quenching of the crystalline phase to room temperature, are underway.

Figure 7:
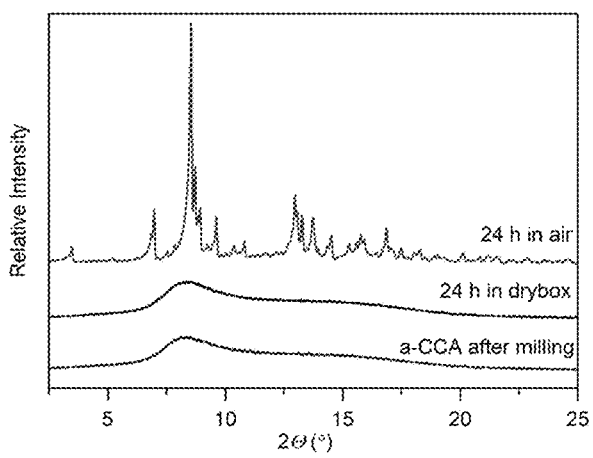
FIG. 7 shows PXRD patterns of a-CCA collected immediately after mechanosynthesis (blue curve), after 24-hr drybox storage (black curve), 24-hr storage under ambient conditions (green curve, transformed into c-CCA).

Next, the inventors tested the behavior of c-CAA and a-CAA exposed to air humidity. The effects of humidity on solid formulations are well-documented in a number of processes, including hydration of anhydrates,[47] polymorphic[48] and amorphous-to-crystalline transformations,[49] and co-crystal syntheses.[50] Water plays a crucial role in the synthesis of c-CAA, and the co-crystal exhibits hygroscopicity physadsorbing water molecules during the milling that can be later removed by aging at room temperature overnight in air (FIG. 3A). On the contrary, a-CAA can be prepared only at dry experimental conditions. To test the effect of humidity on a-CAA, the inventors exposed a freshly prepared co-amorphous sample to ambient humidity for 24 h. As a control experiment, the inventors stored the same amount of sample for 24 h in a drybox. FIG. 7 presents the PXRD patterns of the sample before and after aging at ambient and dry conditions. Stored in a drybox, a-CAA remained amorphous, as evidenced by the diffraction pattern. On the contrary, exposure to ambient humidity led to crystallization of the sample; observed by the sample first becoming wet and then yielding a dry crystalline solid after being dried overnight. Rietveld refinement confirmed that the crystallized sample has the same crystal structure as c-CAA (not depicted). In these experiments, the inventors did not observe deliquescence of a-CAA or c-CAA.

By way of explanation, and in no way a limitation of the present invention, the inventors hypothesized that the humidity-mediated crystallization of a-CAA into c-CAA proceeds in two steps. First, owing to its hygroscopic nature, a-CAA adsorbs water from the air. Next, the regions of a-CAA which are in contact with water molecules exhibit higher molecular mobility, which can be associated with the plasticizing effects of water.[51] The enhanced molecular mobility of creatine and citric acid in the amorphous state allows for local reorganization into the thermodynamically stable local geometry. The well-defined, directional hydrogen-bonding network facilitates an attainment of long-order periodicity and crystallization. Similar effects of moisture-enhanced and amorphous-mediated co-crystallization have been observed for pharmaceutical co-crystals.[52,53]

Figure 8:
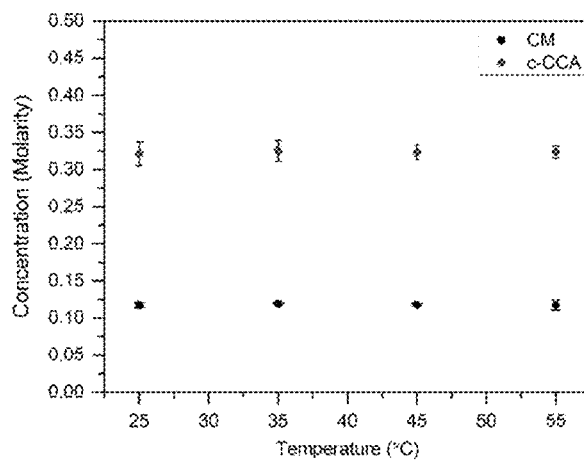
FIG. 8 shows the aqueous solubility of c-CAA and marketed creatine monohydrate presented as the change in molarity as a function of temperature.

Solubility Measurements. The aqueous solubility of c-CAA at room temperature, determined using NMR spectroscopy, is 42.1 g/L. In comparison, the aqueous solubility determined for creatine monohydrate is 13.3 g/L. FIG. 8 presents a plot of the molarity of the c-CAA and creatine monohydrate as a function of temperature. Co-crystallization of creatine with citric acid led to a nearly three-fold improvement of aqueous solubility compared to the marketed creatine monohydrate (13.3 g/L).[3]

In summary, the inventors used a mechanochemical route for the preparation of co-amorphous (a-CAA) and co-crystal (c-CAA) formulations of creatine with citric acid. Ball milling of equimolar amounts of anhydrous reactants in dry conditions leads to the formation of a-CAA, whereas milling in the presence of humidity provides the formation of c-CAA. Water can be introduced in the system as a LAG agent or as a part of the starting materials (either as creatine monohydrate, citric acid monohydrate or a combination of both).

The high crystallinity of c-CAA allowed for ab initio crystal structure solution and Rietveld refinement using the collected powder diffraction data. It was found that the asymmetric unit of the crystal structure consists of one creatine and one citric acid molecule. Close inspection of the intramolecular synthons and the hydrogen donor-acceptor distances between the guanidino and carboxylic groups of neighboring creatine molecules indicated the occurrence of a proton transfer and formation of creatine zwitterions. Citric acid exists in a neutral form, engaging with neighboring citric acid molecules and creatine zwitterions within a well-defined hydrogen-bonded network. The crystal structure solution was further validated by geometry optimization and energy minimization using DFT methods. The experimental and optimized structure of c-CAA were found to be in excellent agreement. To gain further insight into the local structures, a-CAA and c-CAA were studied by vibrational spectroscopy. The IR spectra of the co-amorphous and co-crystal show striking similarities, and therefore conclude that a-CAA adopts a local structure similar to the co-crystal. This conclusion is corroborated by the similar thermal decomposition profiles of both formulations, as observed by TGA. The thermal analyses confirmed that both formulations are anhydrates, consisting of 1:1 molar ratios of creatine and citric acid. Combined TGA and DSC experiments indicate that, upon heating, a-CAA undergoes crystallization before melting and thermal decomposition.

It was found that a-CAA, while stable at dry conditions, readily transforms to c-CAA upon contact with humidity. Metastable amorphous phases have been observed as intermediates in the synthesis of various pharmaceutical co-crystals; moisture-mediated co-crystal synthesis is also well-documented. In this regard, a-CAA can be considered an intermediate phase in the synthesis of c-CAA. Therefore, the isolation and thorough characterization of a-CAA may help better understand the mechanism of co-crystal formation.

Finally, the aqueous solubility of c-CAA was tested by NMR spectroscopy and compared with the solubility of marketed creatine monohydrate. It was found that co-crystallization with citric acid leads to a solubility three-fold higher than that of creatine monohydrate. Thus, c-CAA and similar co-crystals can be marketed as ergogenic aid supplements in the fitness and wellness industry with superior solubility when compared to existing products.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically, and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES (1) Wyss, M; Kaddurah-Daouk R. Creatine and Creatinine Metabolism. Physiological Rev. 2000, 80, 1107-1213.

(2) Kreider, R. B. Effects of creatine supplementation on performance and training adaptations. Mol. Cell. Biochem. 2003, 244, 89-94.

(3) The Merck Index Online. 2020. [online] Available at: <https://www.rsc.org/merck-index> (Accessed 16 Sep. 2020).

(4) Miller, D. W.; Vennerstrom, J. L.; Faulkner, M. C. Creatine oral supplementation using creatine hydrochloride salt. U.S. Pat. No. 7,608,641 B2, Oct. 27, 2009.

(5) Jaeger, R.; Purpura, M.; Shao, A.; Inoue, T.; Kreider, R. B. Analysis of the efficacy, safety, and regulatory status of novel forms of creatine. Amino Acids 2011, 40, 1369-1383.

(6) Jager, R.; Purpura, M.; Ortenburger, G. CREATINE/ CITRIC ACID COMPOUND, METHOD FOR THE PRODUCTION OF THE SAME AND THE USE THEREOF. US 2004/0077719 A1.

(7) Mendel, H; Hodgkin D. C. The crystal structure of creatine monohydrate. Acta Crystallogr. 1954, 7, 443-446.

(8) Arlin, J.-B.; Bhardwaj, R. M.; Johnston, A.; Miller, G. J.; Bardin, J.; MacDougall, F.; Fernandes, P.; Shankland, K.; David, W. I. F.; Florence, A. J. Structure and stability of two polymorphs of creatine and its monohydrate. Cryst. Eng. Comm. 2014, 16, 8197-8204.

(9) Braun, D. E.; Orlova, M.; Griesser, U. J. Creatine: Polymorphs Predicted and Found. Cryst. Growth Des. 2014, 14, 895-4900.

(10) Schultheiss, N.; Newman, A. Pharmaceutical Cocrystals and Their Physicochemical Properties. Cryst. Growth Des. 2009, 9, 2950-2967.

(11) Good, D. J.; Rodríguez-Hornedo. N. Solubility Advantage of Pharmaceutical Cocrystals. Cryst. Growth Des. 2009, 9, 2252-2264.

(12) Duggirala, N. K.; Perry, M. L.; Zaworotko, M. J. Pharmaceutical cocrystals: along the path to improved medicines. Chem. Commun. 2016, 52, 640-655.

(13) Bolla, G.; Nangia, A. Pharmaceutical cocrystals: walking the talk. Chem. Commun. 2016, 52, 8342-8360.

(14) Sander, J. R. G.; Bučar, D.-G.; Henry, R. F.; Zhang, G. G. Z.; MacGillivray, L. R. Pharmaceutical nano cocrystals: sonochemical synthesis by solvent selection and use of a surfactant. Angew. Chem. Int. Ed. 2010, 49, 7284-7288.

(15) Bethune, S. J.; Huang, N.; Jayasankar, A.; Rodríguez-Hornedo, N. Understanding and Predicting the Effect of Cocrystal Components and pH on Cocrystal Solubility. Cryst. Growth Des. 2009, 9, 3976-3988

(16) Babu, N. J.; Nangia, A. Solubility Advantage of Amorphous Drugs and Pharmaceutical Cocrystals. Cryst. Growth Des. 2011, 11, 2662-2679.

(17) Alonzo, D. E.; Zhang, G. G. Z.; Zhou, D.; Gao, Y.; Taylor, L. S. Understanding the behavior of amorphous pharmaceutical systems during dissolution. Mol. Pharmaceutics 2010, 27, 608-618.

(18) Dengale, S. J.; Grohganz, H.; Rades. T.; Löbmann, K. Recent advances in co-amorphous drug formulations. Ad. Drug Delivery Rev. 2016, 100, 116-125.

(19) Braga, D.; Mainia, L.; Grepioni, F. Mechanochemical preparation of co-crystals. Chem. Soc. Rev. 2013, 42, 7638-7648.

(20) Friščić, T. Supramolecular concepts and new techniques in mechanochemistry: cocrystals, cages, rotaxanes, open metal-organic frameworks. Chem. Soc. Rev. 2012, 41, 3493-3510.

(21) Hasa, D.; Rauber, G. S.; Voinovich, D.; Jones, W. Cocrystal Formation through Mechanochemistry: from Neat and Liquid-Assisted Grinding to Polymer-Assisted Grinding. Angew. Chem. Int. Ed. 2015, 127, 7479-7483.

(22) Weyna, D. R.; Shattock, T.; Vishweshwar, P.; Zaworotko, M. J. Synthesis and Structural Characterization of Cocrystals and Pharmaceutical Cocrystals: Mechanochemistry vs Slow Evaporation from Solution. Cryst. Growth Des. 2009, 9, 1106-1123.

(23) Karki, S.; Friščić, T.; Jones, W.; Motherwell, W. D. S. Screening for Pharmaceutical Cocrystal Hydrates via Neat and Liquid-Assisted Grinding. Mol. Pharmaceutics 2007, 4, 347-354.

(24) Halasz, I.; Puškarić, A.; Kimber, S. A. J.; Beldon, P. J.; Belenguer, A. M.; Adams, F.; Honkimäki, V.; Dinnebier, R. E.; Patel, B.; Jones, W.; Štrukil, V.; Friščić, T. Real☐ Time In Situ Powder Xray Diffraction Monitoring of Mechanochemical Synthesis of Pharmaceutical Cocrystals. Angew. Chem. Int. Ed. 2013, 125, 11752-11755.

(25) Friščić, T.; Mottillo, C.; Titi, H. M. Mechanochemistry for Synthesis. Angew. Chem. Int. Ed. 2020, 59, 1018-1029.

(26) Lu, Q.; Zografi, G. Properties of Citric Acid at the Glass Transition. J. Pharm. Sci. 1997, 86, 1374-1378.

(27) Coelho, A. A. Indexing of powder diffraction patterns by iterative use of singular value decomposition. J. Appl. Crystallogr. 2003, 36, 86-95.

(28) Rietveld, H. M. A profile refinement method for nuclear and magnetic structures. J. Appl. Crystallogr. 1969, 2, 65-71.

(29) Pawley, G. S. Unit-cell refinement from powder diffraction scans. J. Appl. Crystallogr. 1981, 14, 357-361.

(30) Cheary, R. W.; Coelho, A. A.; Cline, J. P. Fundamental parameters line profile fitting in laboratory diffractometers. J. Res. Natl. Inst. Stand. Technol. 2004, 109, 1-25.

(31) Andreev, Y. G.; MacGlashan, G. S.; Bruce, P. G. Ab initio solution of a complex crystal structure from powder-diffraction data using simulated-annealing method and a high degree of molecular flexibility. Phys. Rev. B: Condens. Matter Mater. Phys. 1997, 55, 12011-12017.

(32) Dinnebier, R. E. Rigid bodies in powder diffraction. A practical guide. Powder Diffr. 1999, 14, 84-92.

(33) Kohn, W.; Sham, L. J. Self-Consistent Equations Including Exchange and Correlation Effects. Phys. Rev. 1965, 140, A1133-A1138.

(34) Becke, A. D. Density-Functional Exchange-Energy Approximation with Correct Asymptotic Behavior. Phys. Rev. A 1988, 38, 3098-3100.

(35) Lee, C.; Yang, W.; Parr, R. G. Development of the Colle-Salvetti Correlation-Energy Formula into a Functional of the Electron Density. Phys. Rev. B 1988, 37, 785-789.

(36) Civalleri, B.; Zicovich-Wilson, C. M.; Valenzano, L.; Ugliengo, P. B3LYP Augmented with an Empirical Dispersion Term (B3LYP-D*) as Applied to Molecular Crystals. Cryst. Eng. Commun. 2008, 10, 405-410.

(37) Surov, A. O.; Voronin, A. P.; Vener, M. V.; Churakov, A. V.; Perlovich, G. L. Specific Features of Supramolecular Organisation and Hydrogen Bonding in Proline Cocrystals: A Case Study of Fenamates and Diclofenac. Cryst. Eng. Commun. 2018, 20, 6970-6981.

(38) Erba, A.; Maul, J.; Civalleri, B. Thermal Properties of Molecular Crystals Through Dispersion-Corrected Quasi-Harmonic Ab Initio Calculations: The Case of Urea. Chem. Commun. 2016, 52, 1820-1823.

(39) Peintinger, M. F.; Oliveira, D. V.; Bredow, T. Consistent Gaussian Basis Sets of Triple-Zeta Valence with Polarization Quality for Solid-State Calculations. J. Comput. Chem. 2012, 34, 451-459.

(40) Dovesi, R.; Erba, A.; Orlando, R.; Zicovich-Wilson, C. M.; Civalleri, B.; Maschio, L.; Rerat, M.; Casassa, S.; Baima, J.; Salustro, S.; Kirtman, B. Quantum-Mechanical Condensed Matter Simulations with CRYSTAL. WIREs Comput. Mol. Sci. 2018, 8, e1360.

(41) Monkhorst, H. J.; Pack, J. D. Special Points for Brillouin-zone Integrations. Phys. Rev. B 1976, 13, 5188-5192.

(42) Runčevski, T.; Petruševski, G.; Makreski, P.; Ugarkovic, S.; Dinnebier, R. E. On the hydrates of codeine phosphate: the remarkable influence of hydrogen bonding on the crystal size. Chem. Commun. 2014, 50, 6970-6972.

(43) Etter, M. C. Encoding and decoding hydrogen-bond patterns of organic compounds. Acc. Chem. Res. 1990, 23, 120-126.

(44) Aaköry, C. B.; Fasulo, M. E.; Desper, J. Cocrystal or Salt: Does It Really Matter? Mol. Pharmaceutics 2007, 4, 317-322.
(45) Trask, A. V. An Overview of Pharmaceutical Cocrystals as Intellectual Property. Mol. Pharmaceutics 2007, 4, 301-309.
(46) Cruz-Cabeza, A. J. Acid-base crystalline complexes and the pKa rule. Cryst. Eng. Commun. 2012, 14, 6362-6365.
(47) Pirttimaki, J.; Laine, E. The Transformation of Anhydrate and Hydrate Forms of Caffeine at 100-Percent RH and 0-Percent RH. Eur. J. Pharm. Sci. 1994, 1, 203-208.
(48) Yoshinari, Y.; Forbes, R. T.; York, P.; Kawashima, Y. Moisture Induced Polymorphic Transition of Mannitol and Its Morphological Transformation. Int. J. Pharm. 2002, 247, 69-77.
(49) Andronis, V.; Yoshioka, M.; Zografi, G. Effects of Sorbed Water on the Crystallization of Indomethacin from the Amorphous State. J. Pharm. Sci. 1997, 86, 346-351.
(50) Jayasankar, A.; Good, D. J.; Rodríguez-Hornedo, N. Mechanisms by Which Moisture Generates Cocrystals. 2007, 4, 360-372.
(51) Hancock, B. C.; Zografi, G. The Relationship between the Glass-Transition Temperature and the Water-Content of Amorphous Pharmaceutical Solids. Pharm. Res. 1994, 11, 471-477.
(52) Jayasankar, A.; Somwangthanaroj, A.; Shao, Z. J.; Rodríguez-Hornedo, N. Cocrystal Formation During Cogrinding and Storage Is Mediated by Amorphous Phase. Pharm. Res. 2006, 23, 2381-2392.
(53) Seefeldt, K.; Miller, J.; Alvarez-Núñez, F.; Rodríguez-Hornedo, N. Crystallization Pathways and Kinetics of Carbamazepine-Nicotinamide Cocrystals from the Amorphous State by in-Situ Thermomicroscopy, Spectroscopy and calorimetry Studies. J. Pharm. Sci. 2007, 96, 1147-1158.

What is claimed is:

1. A co-crystal of creatine and citric acid obtained by milling, wherein a powder X-ray diffraction (PXRD) diffractogram which peaks at ±3 in °2θ are of a structure with a unit cell parameters a=23.79 Å, b=5.23 Å, c=11.87 Å, α=90°, β=78.5°, γ=90° and space group $P2_1/c$, with selected peaks at °2θ of 1.72, 3.47, 6.85, 6.97, 8.55, 8.71, collected using X-ray radiation with 0.7 Å wavelength.

2. The co-crystal of claim 1, wherein the co-crystal has at least one of a PXRD diffractogram substantially similar to the PXRD diffractogram as depicted in FIG. 1 collected using an X-ray radiation with 0.7 Å wavelength; a DSC thermogram comprising an endothermic peak with a peak onset of approximately 115° C. and a peak maximum of about 126° C., similar to the DSC thermogram as depicted in FIG. 6; or an IR spectrum as depicted in FIGS. 2B and 2C.

3. The co-crystal of claim 1, wherein the creatine is creatine base, creatine anhydrate, creatine in zwitterionic form or creatine hydrate with molar amount of water from 0 to 5; or the citric acid is citric acid anhydrate, or citric acid hydrate with molar amount of water from 0 to 5.

4. The co-crystal of claim 1, wherein a molar ratio of creatine and citric acid is 0.9:1.1, 1:1, or 1.1:0.9.

5. The co-crystal of claim 1, wherein the co-crystal comprises sufficient water to produce, stabilize, or both, the co-crystal.

* * * * *